United States Patent [19]

Matsui et al.

[11] Patent Number: 5,182,775

[45] Date of Patent: Jan. 26, 1993

[54] METHOD OF PROCESSING RADIOGRAPHIC IMAGE DATA FOR DETECTING A WELDING DEFECT

[75] Inventors: Shigetomo Matsui, Higashiosaka; Masahiro Uenishi, Akashi; Sadao Iuchi, Himeji; Kouji Sugimoto; Kouyu Itoga, both of Kobe; Tetsuzo Harada, Akashi; Kouji Michiba, Kobe; Katsuhiro Onda; Takaaki Okumura, both of Nagoya, all of Japan

[73] Assignees: Kawasaki Jukogyo Kabushiki Kaisha, Kobe; The Chubu Electric Power Co., Inc., Aichi, both of Japan

[21] Appl. No.: 639,872

[22] Filed: Jan. 11, 1991

[30] Foreign Application Priority Data

Jan. 12, 1990 [JP] Japan ................................. 2-003508
Jan. 12, 1990 [JP] Japan ................................. 2-003509

[51] Int. Cl.⁵ ........................ G06K 9/00; G01N 23/02
[52] U.S. Cl. ..................................... 382/8; 358/101; 358/106; 378/58
[58] Field of Search ............... 382/8, 1; 358/101, 106, 358/107; 356/237; 378/58, 59

[56] References Cited

U.S. PATENT DOCUMENTS

| | | | |
|---|---|---|---|
| 4,694,479 | 9/1987 | Bácskai et al. | 378/58 |
| 4,809,308 | 2/1989 | Adams et al. | 378/99 |
| 4,926,452 | 5/1990 | Baker et al. | 378/22 |
| 5,048,094 | 9/1991 | Aoyama et al. | 382/8 |
| 5,058,178 | 10/1991 | Ray | 382/8 |

FOREIGN PATENT DOCUMENTS 49-39477 4/1974 Japan.
59-81544 5/1984 Japan.

OTHER PUBLICATIONS

Davies et al., "Discontinuous Registration of Industrial Radiographs Using Profile Analysis and Piecewise Correlation Techniques," May/Jun. 1990, pp. 425-432.
Koshimizu et al., "Weld Inspection Expert System With Image Processing Environment", 1989, pp. 51-56.
Inoue et al., "Automatic Recognition of Weld Defects in Radiographic Test (Report 1)", vol. 11, No. 2, 1982, pp. 123-132.

Primary Examiner—Leo H. Boudreau
Assistant Examiner—Andrew W. Johns
Attorney, Agent, or Firm—Leydig, Voit & Mayer

[57] ABSTRACT

A radiographic test is conducted on a welded portion of a pipe or the like to form a radiographic image, which is introduced into a computer. Volumetric defects and planar defects in the radiographic image are emphasized and extracted by separate methods to obtain a volumetric candidate defect image and a planar candidate defect image. The candidate defect images are then combined to form a single image in which defects can be easily identified. Features of defects in the images are measured, and a set of interference rules is applied to the measured features. Each inference rule gives a degree of certainty that a defect is of a certain type. The degrees of certainty determined by a plurality of the rules are collated to obtain a total degree of certainty, and the type of a defect is inferred from the total degree of certainty.

9 Claims, 5 Drawing Sheets

FIG. 8a
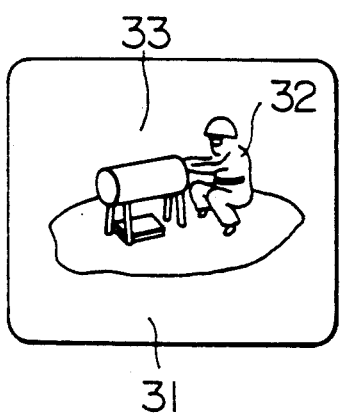
FIG. 8b
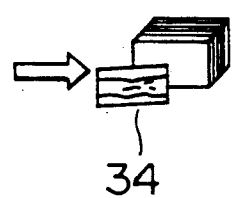
FIG. 8c
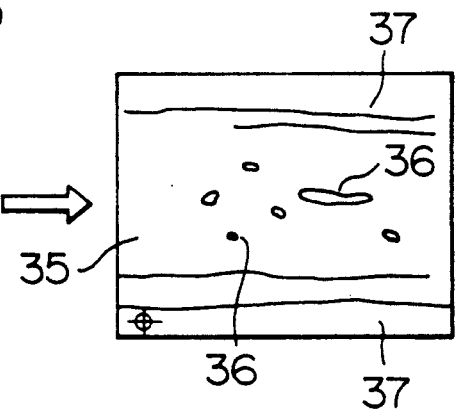
FIG. 8d
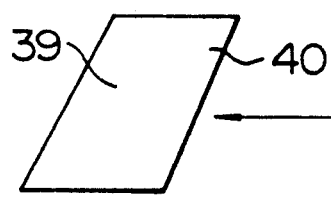
FIG. 8e
FIG. 8f
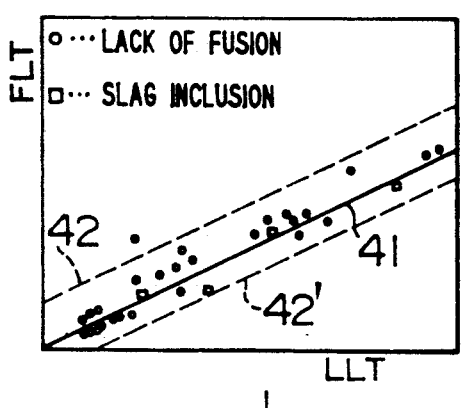
FIG. 8g
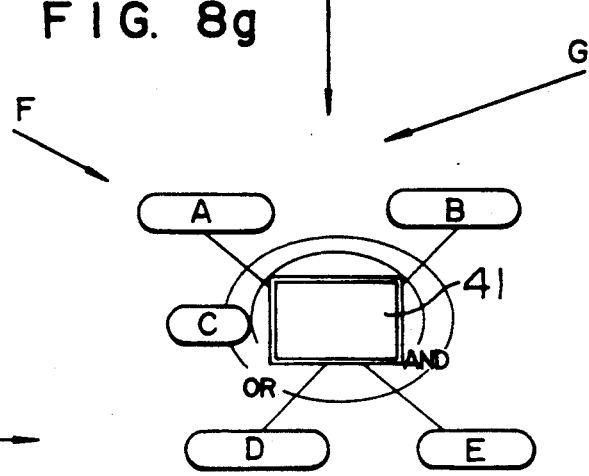

FIG. 9a
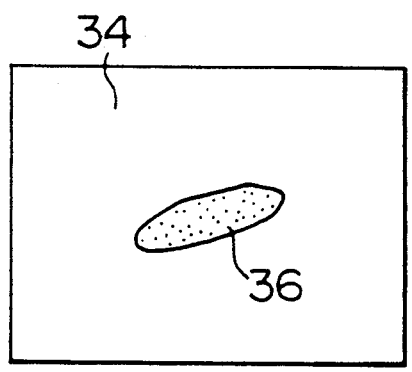
FIG. 9b
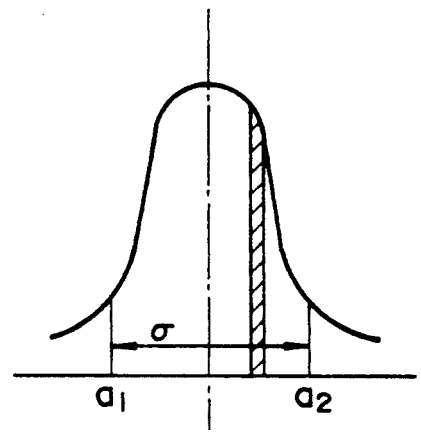
FIG. 9c
FIG. 9d
FIG. 9e
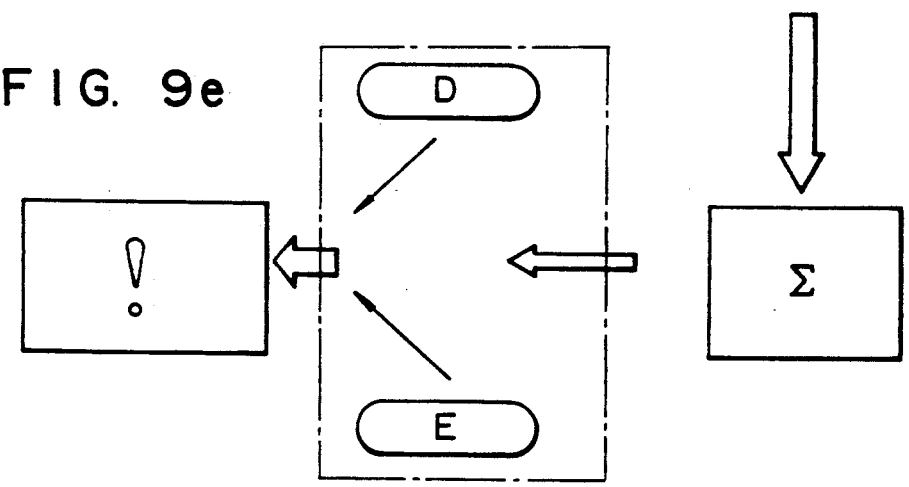

METHOD OF PROCESSING RADIOGRAPHIC IMAGE DATA FOR DETECTING A WELDING DEFECT

BACKGROUND OF THE INVENTION

This invention relates to a method of processing images of welds, and particularly to a method of processing images of welds to detect weld defects in pipes or the like in a power plant facility.

Large machines, plant facilities, etc. include many parts connected by welded portions. These welded portions are often important sections of the facilities.

Welded portions are crucial not only for maintaining the inherent function of a machine, plant facility, etc., but also for maintaining the safety of the machine or facility and of the surrounding environment. Accordingly, welded joints are crucial points of construction, and their maintenance during operation is extremely important.

Large-scale facilities such as power plants and transformer stations, which have strict safety requirements because of their public role, undergo periodic and special maintenance including part replacement, inspection, and tuning under the laws and regulations for electric facilities. When the inspection of internal defect of portions cannot be done in a visual manner or by means of a surface inspection device, a nondestructive inspection method in the form of an X-ray transmission test specified by JIS standards and other standards is frequently employed. The standards also cover the threshold of judgement of a weld defect based on a radiographic test.

However, extremely high proficiency is required of an inspector to make a visual judgement, based on his experience, of an image of a weld defect formed by radiography, so the result of judgement is often lacking in reliability.

Visual inspection and judgement by a skilled inspector rely on a threshold of judgement which can differ depending on the person and can also vary due to visual fatigue and psychological pressure. Therefore, it is difficult to make a stable and objective judgement.

Unless a definite judgement concerning a weld defect is made with high reliability, a further step of maintenance activity cannot be taken, and this situation can impose a serious adverse impact on the operation of a facility and also on its safety.

Therefore, it is extremely desirable for a power plant to be able to automatically evaluate weld defects based on radiography.

A method of automatic defect extraction has been proposed in which an image of a welded joint of a pipe or the like is formed on radiographic film and the developed image is introduced into a computer so that a statistic process can be performed on the image, and the result of the process is used for judgement by an inspector.

An example of a defect extraction method is to categorize defects through the emphasis of defect image by selective application of a computational operator, binary conversion of the emphasized image using a certain threshold, and determination based on the density of the image. This method will be called "the first method" hereinafter.

Another known method is based on the spatial frequency of the density distribution normal to a welding line, in which spectral components of a radiographic image are fed through a band-pass filter to extract a discontinuity at a defective portion. The filter output is subjected to binary conversion based on a certain threshold to identify weld defects. This method will be called "the second method" hereinafter.

A further method employs a signal which is produced by scanning a joint in the direction normal to a welding line. The difference between the signal and its quadratic approximation is subjected to a high-frequency filtering process to emphasize the radiographic image to be subjected to a maximizing process. This method will be called "the third method" hereinafter.

Another known method makes a quadratic curve approximation of the brightness distribution of a radiographic image taken in the direction normal to a welding line and the approximated curve is subtracted from the original curve to produce an emphasized differential image. The image is subjected to binary conversion based on a threshold value derived from the density difference, with the image being modified to clarify the boundary of binary image regions. This method will be called "the fourth method" hereinafter.

In order to infer the type of a weld defect from a radiographic image, a method has been proposed for deterministically classifying the type of weld defect by specifying the existing range of features for each defect type, on the basis of features of the shape of the defect image obtained by image processing of a radiographic image. Also, a method for inferring the type of weld defect from the statistic distribution of features using probability has been proposed. These methods will be called "the fifth method" hereinafter. Examples of this inspection system based on Bayes' law are described in the Proceedings of the Fourth Industrial Image Sensing Technology Symposium, pp. 51-56, entitled "WELD INSPECTION EXPERT SYSTEM WITH IMAGE PROCESSING ENVIRONMENT" by Koshimizu et al. and in the publication Transactions of JWRI, Vol. 11, No. 2, 1982, pp. 123-132, entitled "Automatic Recognition of Weld Defects in Radiographic Test (Report 1)", by Inoue et al.

However, while these conventional methods of extracting a weld defect by an inspector each have advantages, they are impractical for the following reasons.

The first method has the problem that it is difficult to select an operator, i.e., the selection of an operator is not possible unless the image of the defect is known in advance. Since the pixel values of the emphasized image do not have a direct physical meaning, threshold setting must be performed by trial and error. Therefore, there is a high possibility of distortion of an emphasized defect image used for judging defects. Despite the fact that the extracted defect image can possibly include irrelevant indications, this method lacks a processing scheme for eliminating such indications, resulting possibly in oversensitive defect detection.

The second method is capable of extracting a volumetric weld defect such as a blow hole, but it has difficulty extracting a defect image with a small density difference such as a lack of fusion. Since the defect image is discriminated based solely on the extracted density difference, the result of detection is not consistent with that of an experienced human inspector. Therefore, this method is lacking in practicality as an extraction method, and it has the drawback that it is difficult to determine the threshold value.

The third method is deficient in that the defect image cannot be emphasized due to a small density difference for a planar weld defect such as a lack of fusion, as in the second method. Although this method produces a sharp image, it cannot eliminate the density variation at a residual weld portion, and it cannot perform defect image extraction with a single threshold value. The third method by itself is not intended for the automatic extraction of a defect image.

The fourth method is incapable of extracting a defect image with a small density difference such as a lack of fusion. Due to its defect image extraction being based solely on the density difference among pixels of an emphasized image, the sensitivity of detection can differ from that of an experienced inspector. Consequently, it has poor reliability and is inconsistent with the result provided by an inspector because its modification process is based solely on a binary-converted image.

The fifth method proposed by Koshimizu et al. and Inoue et al. involves the following problems. The inspection system proposed by Koshimizu et al. is a determinative method based on a logical sequence, and it is deficient with respect to the addition of new judgement rules and with respect to logical treatment. Although this method is advantageous in the logical processing and measured data processing using graphical data of a weld defect portion and the positions of density around the defective portion, the knowledge of an experienced inspector cannot be introduced or added to the expert system. The system proposed by Inoue et al. uses Bayes' law, and it requires complete data collection. For example, the system needs nine features of a defect, and it does not allow merging with an expert system.

SUMMARY OF THE INVENTION

A first object of this invention is to provide a processing method for automatically extracting a welding defect promptly and accurately from a radiographic film image of a welded portion.

A second object of this invention is to provide a processing method for automatically inferring the type of weld defect promptly and accurately from a radiographic film image of a welded portion.

The first objective of this invention is achieved as follows. A radiographic test is conducted on a welded portion of a pipe in a power plant or the like to produce an image of the welded portion, either on a radiographic film or through an image intensifier. A frame of a picture including an image of the weld defect is introduced into a computer, in which noise is removed, an inspection area is trimmed, and the welding line portion is extracted for preprocessing. Volumetric defects (type 1 defects) and planar defects (type 2 defects) are subjected to specific emphasizing processes. After statistical processing, an extraction process is conducted to discriminate a type 1 defect or type 2 defect. Modification is conducted based on a statistic of the pixel values at the end and peripheral portions of the welding line in the defect-emphasized image of the welding line so that the value is adjusted to correspond to the sensitivity of detection of an inspector, thereby making the result of extraction of the defective portion consistent with that of an experienced inspector. Pixel values of the modified, emphasized image are assumed to have a normal distribution, so that the level of an abnormal image including a defect image can be defined in terms of the standard deviation, and a threshold value for the extraction of a defective portion can be set easily. The knowledge of an experienced inspector for detecting irrelevant indications is prepared as a database, and the features of defects related to the density and shape measured from an extracted defect candidate are compared with the database so as to remove irrelevant indications and avoid oversensitive detection of defect images. Consequently, the ultimate result of judgement of defects is consistent with that of an experienced inspector.

The second objective of this invention attained by making a database of features based on the image on the radiographic film or image intensifier, making a knowledge database of an inspector's experience, making a rule for defect judgement based on both databases, determining the degree of certainty of judgement through the collation of images of welded objects with the rules, and finally inferring the type of welding defect.

BRIEF DESCRIPTION OF THE DRAWINGS

FIGS. 8a to 8g are flowcharts of a second embodiment of this invention, in which:

FIG. 8a illustrates an inspector taking a radiograph of a welded portion;

FIG. 8b is a perspective view of films formed in the process of FIG. 8a;

FIG. 8c is a model of a film;

FIG. 8d is another model of an image film;

FIG. 8e conceptually illustrates a memory storing values for features of defects;

FIG. 8f is a graph showing the correlation between various defect features; and

FIG. 8g is a model of the estimation of the degree of certainty by collation of data o defect features with user input information;

FIGS. 9a to 9e illustrate the estimation of the degree of certainty according to a second embodiment of this invention, in which;

FIG. 9a is a model of a film image;

FIG. 9b is a histogram for a defect feature;

FIG. 9c is a model of the accumulation of weighting factors and degrees of certainty of defect features with respect to the standard deviation;

FIG. 9d is a model of the collation of the degree of certainty; and

FIG. 9e is a model of the estimation of the total degree of certainty.

DESCRIPTION OF THE PREFERRED EMBODIMENTS

Figure 1:
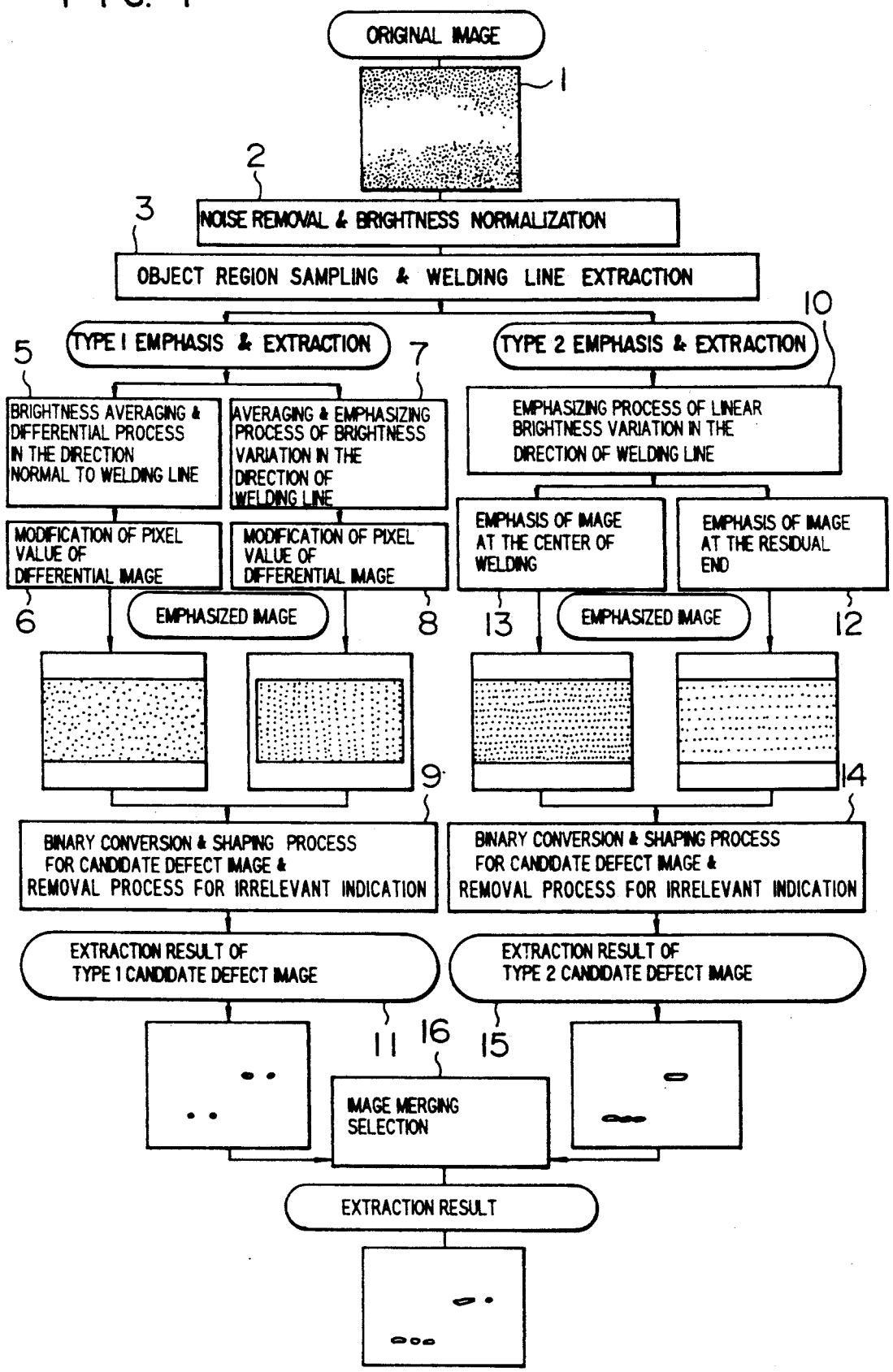
FIG. 1 is a flowchart of a first embodiment of this invention.

A first embodiment of emphasizing and extraction processes according to this invention for enabling the accurate and efficient judgement of a candidate defect image by an inspector will be explained on the flowchart of FIG. 1.

First, a radiographic test using X-rays or the like is conducted for a certain welded portion of a pipe joint or the like in a power plant facility, thereby forming an original image 1 of the welded portion on a radiographic film. The original image on the film is picked up with an ITV (industrial television) camera and introduced into a computer, and at the same time noise in the video signal is eliminated. The reason for the removal of noise is the possible degradation of the picture quality due to noise at the introduction of the film image into the computer through the ITV camera. One noise removal means which can be used is known as a "median filter". This method is to arrange small "window" areas around each point of the image and replace the point with the median brightness of these windows. This process prevents the image from becoming faint due to the noise removal and enables the removal of small data variations and impulse noises in the image without a substantial loss of critical information in the peripheral section. The film image covers, in addition to the welded portion, the base metal and objects outside the base metal such as a transmission meter or a tone meter which are provided to ensure picture quality. The image may also include marks such as letters or numbers for the identification of the film, and the presence of such objects or marks in the image can have a significant influence on the statistic distribution of the brightness of the image, possibly resulting in an inability to emphasize the defective portions in the image. Therefore, in this embodiment, the area of interest in the image is defined so as to extend only as far as images of objects such as the above-mentioned meters and marks in the vertical direction of the welding line. In this manner, the area of interest in the image is sampled (3) and the welding line portion is extracted (4).

A weld defect exists in the region of the welding line. Conceivably, there is a correlation between the frequency of occurrence of certain defects and the position of the defects on the welding line. Accordingly, the extraction of the welding line region is very important. An image of the welding line is divided horizontally into divisions of a proper width, and a binary threshold value is determined automatically based on the least square reference for each divided width. Next, the coordinates of the central point in each column of the binary image are evaluated to determine the center line of the welding line region by application of the method of least squares.

Emphasized extraction of a defect image having a small density difference, such as a lack of fusion, cannot be performed solely by emphasized extraction of a volumetric defect image. To deal with this problem, emphasized extraction for a defect image of type 1, i.e., an image of a volumetric defect such as a blow hole or slag inclusion having a relatively strong contrast and having a thickness in the direction of irradiation by X-rays or other radiation is performed at the sam time as a procedure based on the emphasized extraction for a defect image of type 2, i.e., an image of a planar (linear on the film image) defect having a relatively weak contrast along the welding line, such as a lack of fusion.

The emphasized extraction for a defect image of type 1 is performed by approximating the variation in brightness in the direction normal to the welding line as a quadratic curve, thereby approximating the influence of the brightness of the welding residual portion. Then, a differential process is performed, in which the approximated brightness of the residual portion is subtracted from the original image. The resulting image will be referred to as a differential image.

By this operation, only changes in brightness caused by defective portions will emerge. By using the fact that the change of brightness in the residual portion is gradual compared with the change in brightness due to defects such as blow holes, a quadratic curve calculated by the least squares method is applied to the original image, and the differential image is made as an image, with its contrast of defect being emphasized by subtracting the image with the approximated residual portion from the original image. This differential image has uniform brightness in the background section, and defects appear as dark portions, so even an unskilled inspector can determine the location of defective portions easily.

Next, the modification of pixel value of the differential image is conducted (process 6 in FIG. 1). The reason for the modification is that identical defects appear different in brightness in the central portion and peripheral portion of the welding line. In the case of visual inspection by an inspector, a psychological adjustment of sensitivity is thought to take place so that the central portion and peripheral portion of the welding line are sensed by the inspector as having the same brightness. According to this invention, a statistic of the brightness of the differential image is taken to implement a process equivalent to the inspector's behavior so that the central portion and peripheral portion have equal sensitivity of brightness in terms of the degree of variance, and the same result as obtained by human inspection is realized.

Figure 2:
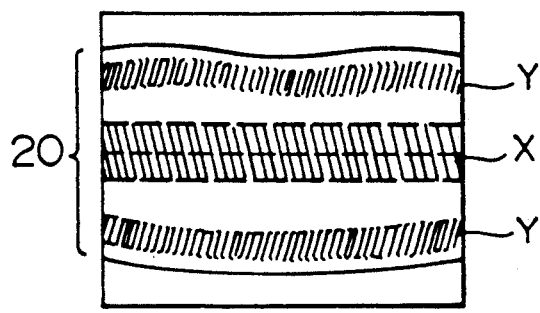
FIG. 2 is a model of a sampling area for modification of pixel values of a differential image.

The region in which the statistic of the overall image is evaluated is confined to the interior of the welding line 20 as shown in FIG. 2 so that a statistic which is unrelated to the sampling area can be evaluated without the influence of the base metal. Two regions X and Y of FIG. 2 are set so that the statistic in the range is made controllable as a parameter of image processing.

Figure 3:
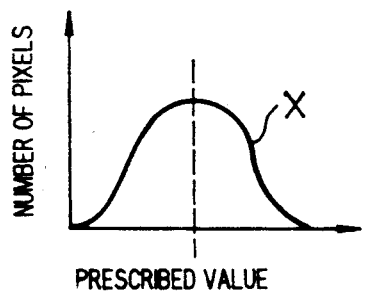
FIG. 3 and 4 are histograms of the number of pixels of certain pixel values in regions a and b in FIG. 2.
Figure 4:
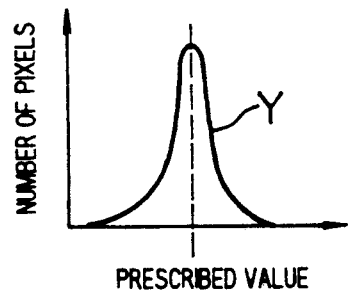

When the statistic of the pixel value in regions X and Y of the differential image is evaluated, it is known that the standard deviation o of the statistic is larger in the central bright portion of the welding line than in the darker boundary portion next to the base metal. Histograms of the number of pixels versus pixel values for regions X and Y of FIG. 2 are shown in FIGS. 3 and 4, respectively. In the differential image, the influence of the brightness change at the residual portion is removed in advance. Therefore, if it is assumed that there is no defect on the welding line and particle noise is evenly distributed on the film, the sensitivity of vision is thought to be adjusted automatically by an inspector in identifying a defect so that the brightness change of the differential image is identified to some extent.

A logarithmic conversion of the brightness is conducted to convert the pixel value to a value which is proportional to the magnitude of a human's visual sensitivity.

The modified pixel value of the defect image is predicated to have been converted to a value which corresponds to the sensitivity of an inspector. Based on this fact, for the modified image, the mean value and standard deviation are evaluated for the statistic of the brightness distribution of the overall image to determine the threshold value by calculating the mean value of brightness minus the standard deviation multiplied by a (where a is a parameter), and pixels having a brightness smaller than or equal to the threshold value are extract as possible defects, which will be referred to a candidate defects (process 9 in FIG. 1). In some cases, a region extracted based on this threshold value can only be an extremely dark portion of the image, and the region is further shaped by expanding it so that pixels with a brightness smaller than or equal to the threshold value plus the standard deviation divided by b (where b is a parameter) in the peripheral portion of the extracted region are included. The result of extraction in this manner is virtually identical to the result of extraction implemented by an inspector.

For the automatic extraction of candidate defects, if it is necessary to have precise measurement of the defect shape on a test film with small variation of bead in the residual portion, a quadratic approximation of the change of brightness in the residual portion is implemented not only in the direction normal to the welding line, but also in the direction of the welding line, as shown in process 7 in FIG. 1. The pixel value of differential image (process 8 of FIG. 1) is modified in the same manner as for the differential image in the direction normal to the welding line, and the resulting modified differential images are merged as a logical sum of the binary images to obtain the region of candidate defects.

In this manner, it is possible to accurately extract a defect image of type 1 without failure.

Images extracted automatically in this manner include irrelevant portions, which are not an inherent defect images or defects other than candidate defects, but are caused by dark shadows or noise or by the influence of special image processing. These irrelevant portions need to be removed.

A characteristic feature of each defect on the film image is measured, and the result is evaluated using removal rules previously stored in a database by an inspector, and based on the evaluation, the irrelevant portions are removed.

Conventionally a defect was determined based on the threshold of brightness. In the present invention, in addition to the brightness and density, characteristic features of defects including the shape and the distribution of brightness and density of a defect and its periphery are employed for screening along with a database of data from a skilled inspector so as to enhance the accuracy of discrimination.

In parallel to the emphasizing and extraction of a volumetric defect image of type 1, the emphasizing and extraction of a defect image of type 2, which is elongated in the lateral direction along the planar welding line such as a lack of fusion, are conducted. First, an emphasizing process for the brightness change in the direction of the welding line is carried out as shown by process 10 in FIG. 1. Because a type 2 defect image has a weaker contrast on the film than a blow hole or other type 1 defect, the use of the same method as for type 1 is inconvenient in that emphasizing is not possible due to the overwhelming brightness of the background.

On this account, for a defect image of type 2, its elongation parallel to the welding line is used to implement a filtering process which emphasizes the brightness conversion along the welding line.

Figure 5A:
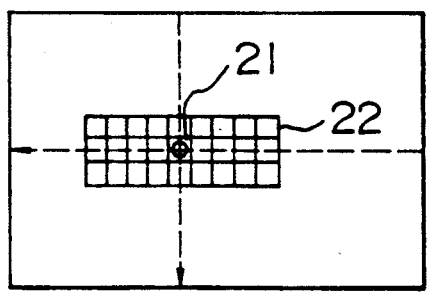
FIGS. 5a and 5b are models of windows for the emphasizing process for a type 2 defect image.

As shown in FIG. 5a, a rectangular window 22 is formed for a pixel 21 of interest at the center, the mean value of brightness in the window 22 is evaluated, and the brightness of the pixel 21 of interest is replaced with the mean value, thereby improving the contrast of a defect image which is elongated in the lateral direction.

Figure 5B:
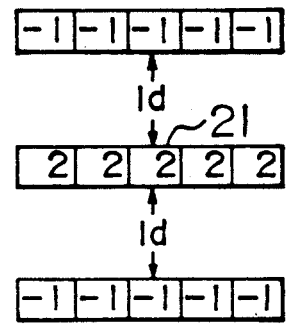

Next, as shown in FIG. 5b, a weighting factor −1 is multiplied by pixels that are distant by id pixels above and below the pixel 21 of interest and a weighting factor of 2 is multiplied by pixels in the central section, and these values are totaled. By conducting a quadratic differential computation process using the total value as the value of the pixel of interest, the component of brightness due to the residual portion is removed, and a defect image which is elongated in the lateral direction is emphasized. The image obtained by the differential computation process will be referred to as a differential image.

For this differential image, emphasizing of the pixel value is conducted in the same manner as for a defect of type 1. First, emphasizing of the image at the end of the residual portion is carried out as shown by process 12 in FIG. 1.

Process 12 implements modification based on logarithmic conversion so that the standard deviation o of the residual end section (low brightness portion) is equal to the standard deviation $\sigma$ of the center section (high brightness portion).

However, implementing such a logarithmic conversion tends to weaken the image in the central section. For example, in the case of a lack of fusion, the contrast is relatively strong along the center line of the welding line in a high brightness portion for which a statistic is to be evaluated, or the image appears to have a large area. Accordingly, the standard deviation $\sigma$ of a high brightness portion becomes much greater than the standard deviation $\sigma$ of a low brightness portion, and as a result of process 12, the sensitivity of the high brightness portion is overwhelmed by that of the low brightness portion, resulting in a failure to emphasize the defect image in the high brightness portion.

In this case, an image which has not been modified by logarithmic conversion of the pixel value is used as an emphasized image at the welding center section in process 13 of FIG. 1.

For the two emphasized images, which have been emphasized in either the residual end section or the welding center section, binary conversion of a candidate defect image, shaping, and irrelevant portion removal shown by process 14 in FIG. 1 are carried out concurrently in the same manner as for a candidate defect image of type I described previously. By combining as a logical sum the binary images obtained by extraction for these defect images of type 2, an extraction result 15 of the candidate defect image of type 2 is obtained.

Finally, combination and selection of the candidate defect image of type 1 and type 2 is performed as shown by process 16.

In the merging and selection for the candidate defect images of type 1 and type 2, when the extraction regions do not overlap, all extracted regions of defect images of type 1 are retained as well as defect images of type 2 having a vertical to horizontal ratio of three or more or a length to width ratio along the inertial main axis of three or more, while the remaining type 2 defect images are removed.

When the extraction regions do overlap, selection is based on the vertical to horizontal ration of the extraction region, on the area or on the distribution of brightness in the extraction region of the original image.

The forgoing irrelevant portion identification is summarized in the following Table 1.

TABLE 1

| Image Type | Basis for discrimination of image information from irrelevant indication |
| --- | --- |
| Candidate defect image of type 1 | • Identify irrelevant indication based on the presence or absence of a density difference between the candidate image and its periphery (above, below, right, left).<br>• Identify typical defect images by strong density contrast (e.g., blow hole).<br>• Identify irrelevant indication based on the position of candidate image (residual end section or welding line central section).<br>• Identify irrelevant indication appearing in parallel along the border line between the residual portion and base metal.<br>• Delete small defects other than dense blow holes. |
| Candidate defect image of type 2 | • Identify irrelevant indication based on the presence or absence of a higher density portion in the candidate image than in the peripheral portion.<br>• Identify typical defects of type 2 (e.g., lack of fusion and faulty connection) based on the length, contrast of density and linearity of candidate image.<br>• Delete defects with small lengths. |

Figure 6:
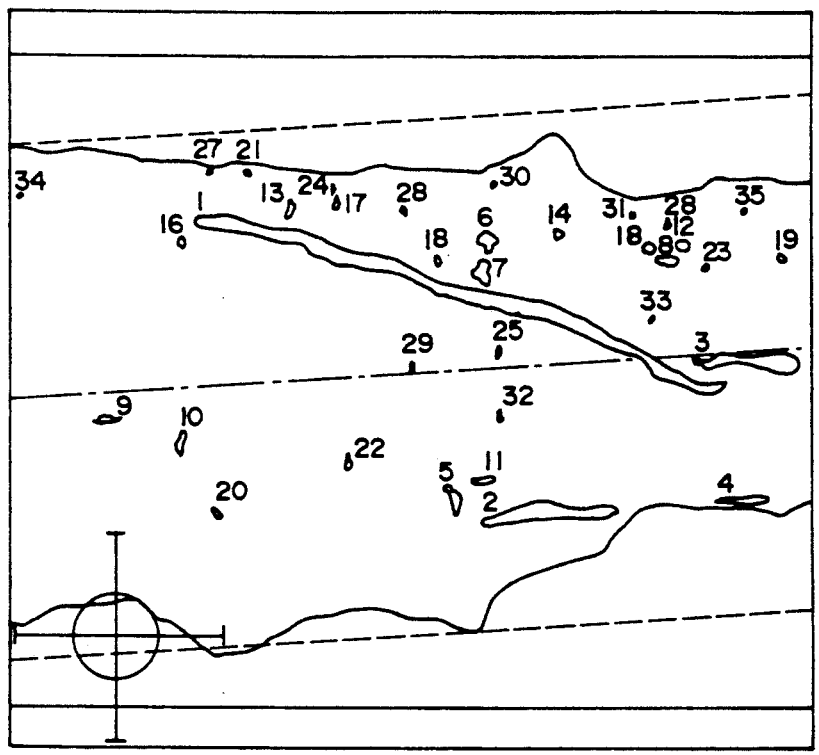
FIG. 6 is a model of a defect candidate image before the application of irrelevant indication removal rules after the extraction of an emphasized image.
Figure 7:
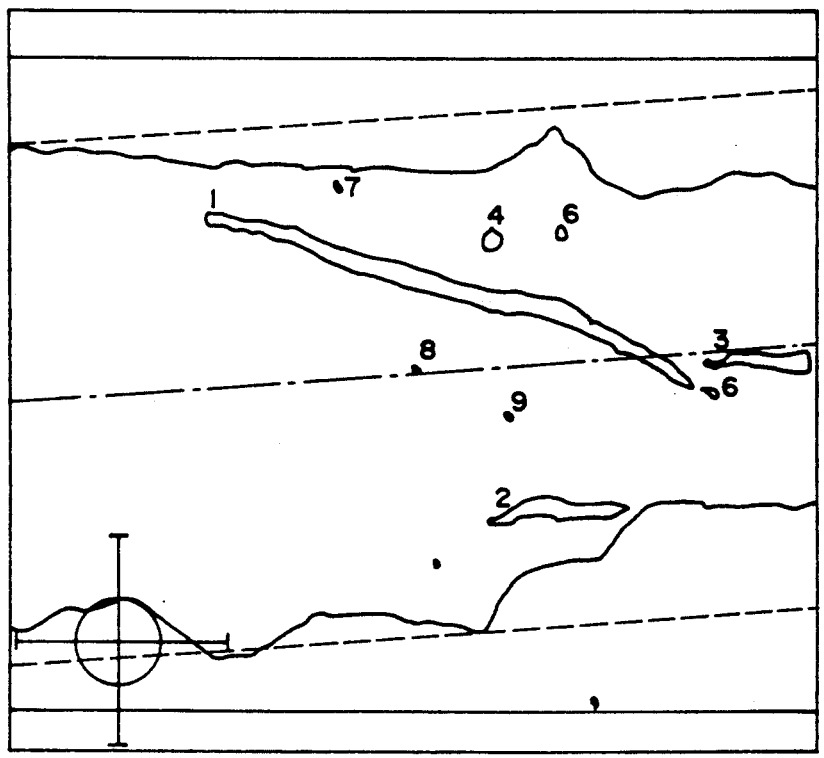
FIG. 7 is a model of the defect candidate image after the application of the irrelevant indication removal rules.

A candidate defect image before the application of the irrelevant indication removal rules given in Table 1 is shown in FIG. 6, and a candidate defect image after the application of the rules is shown in FIG. 7.

The present invention can be applied not only to images formed on radiographic film, but also to images which are introduced directly through an image intensifier.

According to the first embodiment of this invention, for a radiographic test using X-rays or the like for a weld defect such as a blow hole or lack of fusion in a welded portion or the like of a pipe or the like of a power plant facility, it is possible to automatically extract a defective portion and automatically measure the shape and size of the defect, thereby speeding up the inspection and enhancing the repeatability of the result. In addition, the result of extraction is consistent with a result obtained by a human inspector. Setting of the threshold value of extraction is easy, and oversensitive detection of defect images caused by the irrelevant portion removal can by prevented.

By assuming that the distribution of pixel values of modified, emphasized images is a normal distribution, the level of a candidate defect image including a defect image can be defined in terms of the deviation, so setting the threshold value at the time of extraction of the defect image is made easy.

Moreover, by measuring a characteristic feature related to the density and shape of an extracted candidate defect image, and by setting in advance the range of features of a defect image which can be judged to be irrelevant portions by a skilled inspector so that irrelevant portions are removed thoroughly by comparison, oversensitive detection of defect images can be prevented and the efficiency of inspection can be enhanced.

By conducting image emphasizing for a volumetric defect image of type 1 and image emphasizing for a planar defect image of type 2 for the same image, it is possible to eliminate the failure of emphasis of defect images.

Moreover, an emphasized image converted into binary through the calculation of a statistic of pixel values of a modified, emphasized image and subtraction of the threshold value multiplied by a certain parameter of the standard deviation from the mean value so that part of the candidate defect image can be extracted is conceivable to have a virtual normal distribution, an therefore the above-mentioned value of multiple of the standard deviation can be set easily by adjustment in the manner of probability.

For the emphasized image and original image adjacent to the extracted part mentioned above, pixels having lower values than their peripheries are merged and thereafter the border line is smoothed, whereby it is possible to extract the shape of a defect image which is consistent with the result conventionally obtained by human inference, i.e., inference by an inspector of the like having much experience.

Based on the capability of the active use of the knowledge of an inspector in making the judgement of an irrelevant indication in the abnormal image among images in advance, oversensitive detection of defect images can be prevented.

Next, a second embodiment of this invention will be explained. As shown in FIG. 8g, the method of inferring the type of weld defect according to the second embodiment of this invention is as follows. Measured data for a welded portion obtained from an image on radiographic film, the degree of certainty of rules A, B and C of a knowledge database based on features of a weld defect derived from data, and the rule of user input information D and E which can be obtained by experience by only one of a welding worker or an inspector are subjected to collation to obtain a total degree of certainty. Using the degree of certainty, it becomes possible to determine whether a weld defect is a lack of fusion, or to infer the certainty of a defect such as slag inclusion. For the above-mentioned user input information D and E, the welding conditions which are known by a welding worker, e.g., the welding attitude such as up-face welding or down-face welding, the magnitude of welding current, the slag of welding bead, the state of scale, the type of tip-open welding, etc. are added with the degree of certainty based on the experience of the welding worker to make a certain rule in advance. As shown in FIG. 8g, the degree of certainty (F) of a feature of a defect based on measurement of an image of a weld defect and the abovementioned user input information (G) are collated in a total sense, and the result is used together with the total degree of certainty based on a parallel comparison with each rule, and the type of weld defect is inferred. The features of the weld are obtained by a complicated procedure, and a specific procedure of rule generation is as follows. As shown in FIG. 8a, at the site 31 of a piping facility or the like in a power plant, an inspector 32 takes a radiographic film picture of a weld defect in a welded portion of a pipe or the like by means of a radiographic inspection device 33 using X-rays or the like. As shown in FIG. 8b, a resulting image film 34 is developed. As shown in FIG. 8c, it is ascertained that a weld defect portion (including defect candidates) 36, which appears in the image at a bead section 35 of the image film 34, exists between base metals 37, and direct measurement of the weld defect portion 36 on the image film 34 is conducted to obtain input information on the following features of the defects shown in Table 2.

TABLE 2

| | Feature | Abbreviation | Value |
|---|---|---|---|
| 1 | Flatness | (4FLT) | 1.564 |
| 2 | Symmetry | (SYM) | 0.796 |
| 3 | Unsharpness | (USP) | 0.481 |
| 4 | Direction of major axis | (ANG) | 3.340 |
| 5 | Position | (PST) | 0.156 |
| 6 | Average density | (DME) | 0.005 |
| 7 | Density distribution | (DSG) | 0.004 |
| 8 | Major span | (LLT) | 9.319 |
| 9 | Minor span | (SLN) | 0.769 |
| 10 | Nonlinearity | (NOL) | 0.069 |

The average density through the nonlinearity are features employed in this invention. The welding center line 38, defect image 36, angle $\Theta$ and the like for the bead 35 between the base metals 37 on the image film 34 are schematically shown in FIGS. 8c and 8d. From the film image as shown in FIG. 8c and FIG. 8d, numeric values of the features of the weld defect are measured and stored in a memory unit 40 shown in FIG. 8e. In FIG. 8e, 39 represents the values of the features of the weld defect corresponding to the data in Table 2.

Of the features of the weld defect which have been measured by an instrument directly from a film image, there is a specific relationship among certain features, as shown by experience. For example, as shown in FIG. 8f, in which the length of defect (LLT) in mm is plotted on the horizontal axis and the flatness (FLT) is plotted on the vertical axis, there is a linear relationship FLT = ⅓ LLT between the two features, and a specific distribution of lack of fusion portions and slag inclusions above and below the line is obtained. Accordingly, through the arrangement of data of Table 2 for the relation between the defect length (LLT) and flatness (FLT), an identification rule of a knowledge base is created. In the example shown in FIG. 8f, it is determined in advance that if the data satisfies the conditions ⅓ LLT −0.2<FLT<⅓LLT+0.3 and LLT<12, then it is inferred that the weld defect is a lack of fusion or it is a slag inclusion with a degree of certainty of 0.95.

As a method of providing a degree of certainty in this case, the probability for all the data may be used.

Needless to say, the foregoing embodiment is an example of an identification rule using two specific features LLT and FLT of the weld defect portion 36. For other features of the weld defect, other identification rules are available, and a certain number of these rules are used in parallel.

The identification rule F obtained as a knowledge base, the features 39 of the weld defect, and the user input information G and user input information D and E are collated for each rule in a general manner, as shown in FIG. 8g. If the individual degrees of certainty are examined and a specific degree of certainty is given priority over the others, the type of defect and the cause of defect of a certain weld defect portion are inferred. Alternatively, a total degree of certainty is evaluated based on a certain calculation method of the degree of certainty, and the certainty of the type and cause of the weld defect portion is presented as a composite degree of certainty.

Another form of estimation of the degree of certainty based on identification rules using data processing of features of the defective portion on the radiographic image film is shown in FIG. 9a to FIG. 9e.

Rule generation is performed base on data processing as shown in FIG. 9a to FIG. 9c. As shown in FIG. 9a, the features of a defect shown in Table 2 are evaluated in advance for a defective portion 36 of a film image 34. A database for each feature is created in advance, and the feature is compared with the database to determine whether the feature falls into the range of standard deviations $1\sigma$, $2\sigma$, or $3\sigma$. For example, in the case of a blow hole, as shown in FIG. 9b, weighting factors of 1.0, 0.6 and 0.1 are given to the deviations $\sigma$, $2\sigma$, and $3\sigma$, respectively, and the weighting factors are selected to be 1.0, 0.6 and 0.1 as the degree of certainties for the flatness, density and weld defect length, respectively, as shown in the following Table 3. (The weighting factors and degrees of certainty differ depending on the experience of an inspector, so it is desirable to have the weighting factors and degrees of certainty estimated by an inspector who has much skill.)

TABLE 3

| | $\sigma$ | $2\sigma$ | $3\sigma$ | Certainty of results |
|---|---|---|---|---|
| Weighting factor | 1.0 | 0.6 | 0.1 | |
| Flatness | ○ | | | 1.0 |
| Density | | ○ | | 0.6 |
| Length of defect | | | ○ | 0.1 |

Calculation of the degree of certainty based on the weighting factor is conducted for each feature of the defect, and by merging the result with the degree of certainty of the user input information, the ultimate degree of certainty is determined in the same manner as described previously.

Needles to say, the knowledge base can have a structure different from that in the second embodiment.

For the user input information, the degree of certainty can be obtained in advance by means of an interview or the like with a welding worker or welding inspector.

Through the collation of the parallel set of identification rules of the knowledge base, the type and cause of a weld defect are expressed by a rule system such as "if...then...", and the degree of certainty is...", thereby estimating the inference of certainty in a sense of fuzzy theory by avoiding the assertion of the type and cause in a sense of determinative theory.

Needless to say, in the case of a plurality of degrees of certainty as a result of collation of a plurality of identification rules, as mentioned previously, a final, total degree of certainty is estimated base on a certain calculation method of the degree of certainty.

The procedure is shown n FIGS. 9c, 9d and 9e.

Embodiments of this invention are not limited to use with radiographic images of a welded portion on film, and the image may be introduced as a direct digital image through an image intensifier or displayed on a CRT.

According to the second embodiment of this invention, the certainty which is not obtained by the conventional method is inferred and the error made by the determinative method can by avoided, whereby the degree of certainty which is closed to the inference of the type and cause of a practical defective portion implemented by an extremely expert inspector can be estimated. In addition, it is very easy to add a new rule or alter a rule, complete supplement for the collected data is not needed, and inference based on data which can be collected is made possible.

By using ten features of a defect and user input information provided by a skilled inspector in addition to the dimensions and complexity of the graphical feature of the defect and the density and position of its periphery, inference which very closely approximates the inference by an experienced inspector can be attained. Also, it provides the flexibility of replacing the degree of certainty based on the variance or other statistic of the feature derived from actual data.

Furthermore, in some cases, the present invention has the capability of including information other than information on the features of a defect.

We claim:

1. A method of processing radiographic image data comprising:
   forming a radiographic image of a welded portion including a welding line;
   digitizing the radiographic image to form image data;
   performing a first differential process on the image data to obtain first differential image data corresponding to a volumetric defect image in the radiographic image;
   calculating a first threshold;
   extracting pixels having a brightness less than the first threshold from the first differential image data to obtain first candidate defect image data;
   performing a second differential process on the image data to obtain second differential image data corresponding to a planar defect image in the radiographic image;
   calculating a second threshold;
   extracting pixels having a brightness less than the second threshold from the second differential image data to obtain second candidate defect image data;
   merging the first and second candidate defect image data to obtain merged image data; and
   displaying the merged image data.

2. A method as claimed in claim 1 wherein the first differential process comprises:
   approximating a brightness of a residual portion of the radiographic image surrounding the welding line by a quadratic approximation which varies in a direction normal to the welding line; and
   subtracting the approximated brightness from the image data.

3. A method as claimed in claim 1 wherein performing the second differential process comprises:
   forming a rectangular window elongated in the direction of the welding line around a pixel of interest in the image data;
   replacing a brightness of the pixel of interest with a mean brightness of the window;
   multiplying the brightness of the pixel of interest by a first weighting factor to obtain a first weighted brightness;
   multiplying the brightness of a pixel separated from the pixel of interest in the direction normal to the welding line by a second weighting factor to obtain a second weighted brightness;
   forming a total brightness from the first and second weighted brightnesses; and
   replacing the brightness of the pixel of interest with a value based on the total brightness.

4. A method as claimed in claim 1 further comprising:
   approximating a brightness in a welding residual portion surrounding the welding line by a quadratic approximation which varies in the direction of the welding line;
   subtracting the approximated brightness from the image data to obtain third differential image data; and
   combining the third differential image data with the first differential image data prior to extracting pixels based on the first threshold.

5. A method as claimed in claim 1 further comprising:
   emphasizing data in the second differential image data corresponding to a center of the welding line to obtain first emphasized image data;
   emphasizing data in the second differential image corresponding to a residual end portion to obtain second emphasized image data; and
   combining the first and second emphasized image data.

6. A method as claimed in claim 1 further comprising removing irrelevant indications by measuring a feature of a defect in the first and second candidate defect image data and comparing the measured feature with a database based on the experience of an inspector.

7. A method of inferring the type of a weld defect comprising:
   forming a knowledge base comprising a plurality of defect inference rules;
   measuring a feature of a weld defect of interest in a radiographic image of a weld;
   applying a plurality of the defect inference rules to the measured feature to calculate, for each applied rule, a probability that the weld defect of interest is of a certain type;
   collating all the calculated probabilities to obtain a total probability; and
   inferring the type of the weld defect of interest based on the total probability.

8. A method as claimed in claim 7 wherein calculating the probability for each applied rule comprises:
   calculating a mean value of a defect feature for a specific type of weld defect;
   establishing a plurality of ranges with respect to the mean value; and
   assigning the measured feature of the weld defect of interest a probability based on which of the ranges contains the measured feature.

9. A method of inferring the type of a weld defect comprising:
   measuring a plurality of features of weld defects in a radiographic image;
   forming a database of the measured features;
   forming a knowledge base comprising a plurality of defect inference rules, each of which corresponds to one or more defect features and gives a probability that a defect is of a certain type;
   forming a knowledge base of user input information related to welding conditions;
   applying one or more of the inference rules to one of the measured features of a defect of interest in the radiographic image to determine a probability that the defect of interest is a specific type of defect;
   collating the probability with the user input information to obtain a total probability; and
   inferring the type of the defect of interest from the total probability.

* * * * *